US012642574B2

(12) United States Patent
Murdeshwar

(10) Patent No.: US 12,642,574 B2
(45) Date of Patent: Jun. 2, 2026

(54) MEDICAL INSTRUMENT CUTTING SYSTEMS AND METHODS

(71) Applicant: GYRUS ACMI, INC., Westborough, MA (US)

(72) Inventor: Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 544 days.

(21) Appl. No.: 17/306,150

(22) Filed: May 3, 2021

(65) Prior Publication Data

US 2021/0346084 A1     Nov. 11, 2021

Related U.S. Application Data

(60) Provisional application No. 63/020,831, filed on May 6, 2020.

(51) Int. Cl.
*A61B 17/42*          (2006.01)
*A61B 17/32*          (2006.01)
(Continued)

(52) U.S. Cl.
CPC .............. *A61B 18/14* (2013.01); *A61B 90/30* (2016.02); *A61B 2017/00318* (2013.01);
(Continued)

(58) Field of Classification Search
CPC ................... A61B 18/14; A61B 90/30; A61B 2017/00907; A61B 2017/4225;
(Continued)

(56) References Cited

U.S. PATENT DOCUMENTS 5,209,754 A * 5/1993 Ahluwalia ......... A61B 17/4241
                                                        606/1
5,613,950 A * 3/1997 Yoon ....................... A61F 13/38
                                                        604/105
(Continued)

FOREIGN PATENT DOCUMENTS

AU          2016228311 A1 * 10/2016 ............. A61B 17/42
CN          113616300 A      11/2021
(Continued)

OTHER PUBLICATIONS

"European Application Serial No. 21170311.1, Extended European Search Report mailed Oct. 7, 2021", 7 pgs.
(Continued)

*Primary Examiner* — Joseph A Stoklosa
*Assistant Examiner* — Ana Veruska Guerrero
(74) *Attorney, Agent, or Firm* — Schwegman Lundberg & Woessner. P.A.

(57) ABSTRACT

An end effector assembly of a tissue resection device may include a first cut guide including a first support surface that extends from a first proximal end portion to a first distal end portion including a first outer distal portion, and a second cut guide located around the first cut guide. The second cut guide may include a second support surface that extends from a second proximal end portion to a second distal end portion having a second outer distal portion. The first outer distal portion may be located distal of the second outer distal portion and the first outer distal portion may also be located farther laterally from the longitudinal axis than the second outer distal portion. The end effector assembly may also include a cutting device located between the first and second cut guides.

19 Claims, 10 Drawing Sheets

(51) Int. Cl.

| | |
|---|---|
| *A61B 18/14* | (2006.01) |
| *A61B 90/30* | (2016.01) |
| *A61B 17/00* | (2006.01) |
| *A61B 17/3207* | (2006.01) |
| *A61B 17/34* | (2006.01) |
| *A61B 18/00* | (2006.01) |

(52) U.S. Cl.
CPC .............. *A61B 2017/00327* (2013.01); *A61B 2017/00367* (2013.01); *A61B 2017/00907* (2013.01); *A61B 2017/320074* (2017.08); *A61B 17/320092* (2013.01); *A61B 2017/320093* (2017.08); *A61B 17/320725* (2013.01); *A61B 17/320758* (2013.01); *A61B 17/320783* (2013.01); *A61B 17/3403* (2013.01); *A61B 2017/4216* (2013.01); *A61B 2017/4225* (2013.01); *A61B 17/4241* (2013.01); *A61B 2018/00077* (2013.01); *A61B 2018/00083* (2013.01); *A61B 2018/00559* (2013.01); *A61B 2018/00601* (2013.01)

(58) Field of Classification Search
CPC ........... A61B 2018/00077; A61B 2018/00083; A61B 2018/00559; A61B 2018/00601; A61B 18/1402; A61B 17/42; A61B 2017/00477; A61B 2017/00876; A61B 2017/00902; A61B 2017/00929; A61B 2017/320052; A61B 2018/146; A61B 18/12; A61B 2018/00577; A61B 2018/1253

See application file for complete search history.

(56) References Cited

U.S. PATENT DOCUMENTS

| | | | | |
|---|---|---|---|---|
| 6,050,992 A | * | 4/2000 | Nichols | .............. A61B 18/1477 606/49 |
| 6,126,656 A | | 10/2000 | Billings | |
| 8,323,278 B2 | | 12/2012 | Brecheen et al. | |
| 9,144,454 B2 | | 9/2015 | Batchelor et al. | |
| 9,439,677 B2 | | 9/2016 | Germain et al. | |
| 9,554,853 B2 | | 1/2017 | Strul et al. | |

| | | | | |
|---|---|---|---|---|
| 10,130,389 B2 | | 11/2018 | Sullivan et al. | |
| 11,090,082 B2 | * | 8/2021 | Weihe | ................ A61B 18/1485 |
| 2001/0021854 A1 | * | 9/2001 | Donnez | .............. A61B 17/4241 606/119 |
| 2005/0187561 A1 | * | 8/2005 | Lee-Sepsick | .... A61B 17/12186 606/108 |
| 2007/0225702 A1 | * | 9/2007 | Kaouk | .......... A61B 17/320016 606/49 |
| 2012/0109124 A1 | * | 5/2012 | Morozov | .......... A61B 17/4241 606/41 |
| 2012/0143209 A1 | | 6/2012 | Brecheen et al. | |
| 2012/0165826 A1 | | 6/2012 | Rhemrev-pieters | |
| 2014/0276916 A1 | * | 9/2014 | Ahluwalia | ........ A61M 25/0068 606/119 |
| 2015/0133923 A1 | * | 5/2015 | Batchelor | .......... A61B 18/1482 606/48 |
| 2015/0351621 A1 | * | 12/2015 | Hill | ........................ A61B 17/42 600/249 |
| 2017/0071781 A1 | * | 3/2017 | Skalnyi | .............. A61B 18/1485 |
| 2017/0112535 A1 | * | 4/2017 | Ahluwalia | ......... A61B 17/4241 |
| 2017/0156756 A1 | * | 6/2017 | Adajar | ................... A61B 18/10 |
| 2017/0325844 A1 | | 11/2017 | Prior | |
| 2018/0140756 A1 | | 5/2018 | Klein et al. | |
| 2018/0168667 A1 | | 6/2018 | Germain et al. | |
| 2018/0325575 A1 | * | 11/2018 | Begg | ................. A61B 18/1206 |
| 2019/0167306 A1 | | 6/2019 | Brecheen et al. | |

FOREIGN PATENT DOCUMENTS

| | | | | | |
|---|---|---|---|---|---|
| EP | 3400894 A2 | * | 11/2018 | ....... | A61B 17/32002 |
| EP | 3205298 B1 | | 5/2020 | | |
| WO | WO-9917837 A1 | * | 4/1999 | .......... | A61N 1/0524 |
| WO | WO-2009073619 A2 | * | 6/2009 | ......... | A61B 17/0469 |
| WO | WO-2010151429 A2 | | 12/2010 | | |
| WO | WO-2012114334 A1 | * | 8/2012 | ......... | A61B 1/00087 |
| WO | WO-2019040542 A1 | * | 2/2019 | ....... | A61B 17/00234 |
| WO | WO-2022051260 A2 | * | 3/2022 | | |

OTHER PUBLICATIONS

"European Application Serial No. 21170311.1, Response filed May 6, 2022 to Extended European Search Report mailed Oct. 7, 2021", w/ Claims, 7 pgs.

* cited by examiner

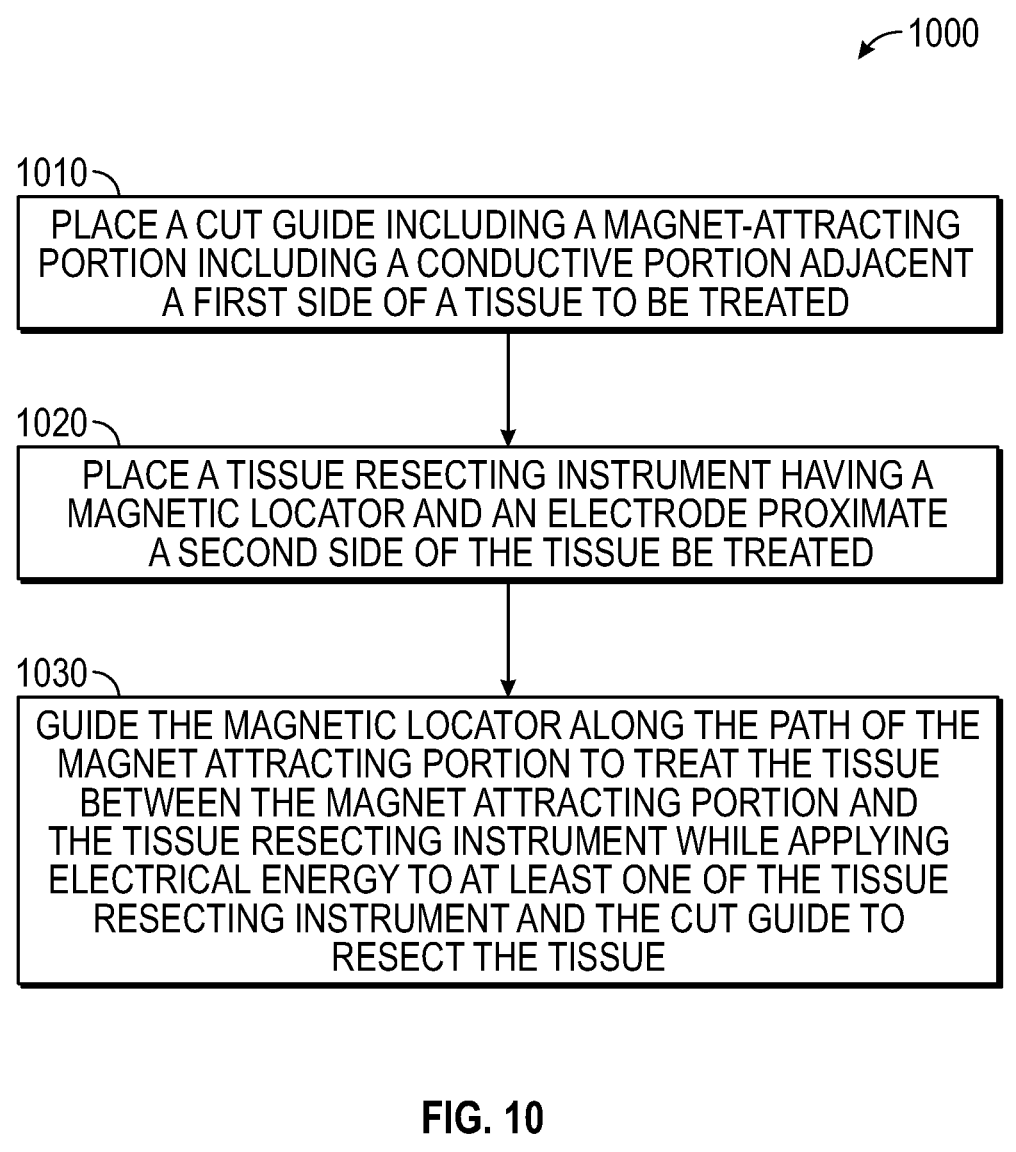

1000

1010
PLACE A CUT GUIDE INCLUDING A MAGNET-ATTRACTING PORTION INCLUDING A CONDUCTIVE PORTION ADJACENT A FIRST SIDE OF A TISSUE TO BE TREATED

1020
PLACE A TISSUE RESECTING INSTRUMENT HAVING A MAGNETIC LOCATOR AND AN ELECTRODE PROXIMATE A SECOND SIDE OF THE TISSUE BE TREATED

1030
GUIDE THE MAGNETIC LOCATOR ALONG THE PATH OF THE MAGNET ATTRACTING PORTION TO TREAT THE TISSUE BETWEEN THE MAGNET ATTRACTING PORTION AND THE TISSUE RESECTING INSTRUMENT WHILE APPLYING ELECTRICAL ENERGY TO AT LEAST ONE OF THE TISSUE RESECTING INSTRUMENT AND THE CUT GUIDE TO RESECT THE TISSUE

FIG. 10

MEDICAL INSTRUMENT CUTTING SYSTEMS AND METHODS

CROSS-REFERENCE TO RELATED APPLICATION

This application claims the benefit of U.S. Provisional Patent Application Ser. No. 63/020,831 filed May 6, 2020, the content of which is incorporated by reference herein in its entirety.

TECHNICAL FIELD

This document pertains generally, but not by way of limitation, to surgical instruments and methods related to guiding cutting elements and excising tissue in medical procedures. More specifically, but not by way of limitation, the present disclosure can be used with systems and methods for a tissue resection device, such as an end effector assembly for performing a colpotomy.

BACKGROUND

Many surgical procedures involve the treatment or removal of subdermal target tissue, e.g., diseased or unwanted tissue or growths, located inside of a patient. As such, these procedures require access to and visibility of the internal anatomy of the patient.

The anatomy of the female reproductive system includes, among other things, ovaries, fallopian tubes, a uterus, a cervix and a vagina. As a result of certain gynecological conditions, such as cancers or severe pain and heavy bleeding, it sometimes becomes necessary to treat a patient's uterus. One option for treating the uterus includes surgically removing the uterus via a hysterectomy procedure.

One hysterectomy procedure is known as a total hysterectomy and involves the complete removal of a patient's uterus and cervix. Initially, hysterectomy procedures were performed via an incision in a patient's abdomen. With advancement in surgical tools and procedures, hysterectomy procedures have evolved to include vaginal and laparoscopic techniques. Today, hysterectomy procedures involve one of four primary approaches: total abdominal hysterectomy (TAH), total vaginal hysterectomy (TVH), total laparoscopic hysterectomy (TLH), and laparoscopic supracervical hysterectomy (LSH).

Medical literature has shown that the TLH and LSH can be useful over the conventional TAH and TVH approaches. The TLH and LSH approaches can be desirable because of several potential benefits, including, for example, less postoperative pain, shorter hospital stays, and faster recovery times. It may be beneficial if more hysterectomies performed each year were performed via the TLH or LSH approach. Often, the reasons for performing a hysterectomy without using a TLH or LSH approach include the limitations of laparoscopic surgery in general.

Limitations with performing hysterectomies, and laparoscopic hysterectomies in particular can include limited visibility, difficulty in manipulating internal organs, and a tendency of a cutting device to "wander" during the cauterization/cutting procedure known as a colpotomy, used to excise the uterus. These challenges can also be present in non-laparoscopic hysterectomies and other surgeries as well.

A colpotomy is a procedure by which an incision is made in the vagina, to perform a hysterectomy, to gain access to visualize other pelvic structures, or to perform a surgery on the fallopian tubes or ovaries. To perform a colpotomy, a surgeon guides an medical instrument including an end effector assembly located at a distal end, through the vaginal opening into the into a vagina of the patient and positions a cutting guide of the end effector assembly proximate a surgical site. The cutting guide can be used to guide a cutting device for performing an incision through the vagina proximate to and around the cervix. Performing a colpotomy can be a difficult procedure for a surgeon, because other tissues, such as the bowel (e.g., rectum, colon) and bladder are located in close proximity to the colpotomy incision site in the vaginal wall. Accordingly, there is a need for improved instruments, systems and methods for performing surgeries, including, but not limited to, surgeries that require a colpotomy procedure.

Overview

The present inventor has recognized, among other things, that problems to be solved in performing tissue resection procedures such as a colpotomy, include a surgeon being able to easily insert an end effector assembly into a vagina of a patient and move the end effector assembly toward the cervix with less force. Furthermore, the present inventor has recognized that surgeons have challenges with gaining visual access to identify pelvic anatomy and facilitate surgical dissection. Yet further, the present inventor has recognized that surgeons have challenges with accurately guiding and controlling a cutting device in surgical procedures, such as a colpotomy procedure performed during a total laparoscopic hysterectomy (TLH). The inventor has also recognized that improvements in conventional cutting devices are needed to improve visibility of the cut location as well as an improvement in the transmission of light to the area around or through a cutting element. Additionally, the inventor has recognized a need to better focus and control electrical energy applied to a tissue while minimizing damage to adjacent tissue. The present subject matter can provide solutions to these problems and other problems.

In an example, a medical instrument such as a tissue resection device can comprise an elongate member including a body that extends from a proximal portion to a distal portion and a lumen extending therebetween, a handle that is coupled to the proximal portion, and an end effector coupled to the distal portion, the end effector extending along a longitudinal axis. The end effector can include: a first cut guide including an outer support surface that extends from a first proximal end portion to a first distal end portion, and the first distal end portion includes a first outer distal portion; a second cut guide located around the first cut guide, the second cut guide having an inner support surface that extends from a second proximal end portion to a second distal end portion, and the second distal end portion includes a second outer distal portion. Further, the first outer distal portion can be located distal of the second outer distal portion, and the first outer distal portion can be located farther laterally from the longitudinal axis than the second outer distal portion. The end effector can further include a cutting device located between the outer support surface and the inner support surface, and a cutting device actuator configured to actuate movement of at least a portion of the cutting device to protrude beyond the first outer distal portion and the second outer distal portion, wherein the cutting device can be movable in a direction having a longitudinal component and a lateral component when actuated.

In an example, an end effector assembly of a tissue resection device can comprise a first cut guide that extends from a first proximal end portion to a first distal end portion along a longitudinal axis, and the first distal end portion can include a first outer distal portion; a second cut guide located around the first cut guide, the second cut guide can extend from a second proximal end portion to a second distal end portion, and the second distal end portion can include a second outer distal portion. Further, the first outer distal portion can be located distal of the second outer distal portion, and the first outer distal portion can be located farther laterally from the longitudinal axis than the second outer distal portion. A cutting device can be located between the first cut guide and the second cut guide, and the cutting device can be configured to move relative to at least one of the first cut guide and the second cut guide when actuated.

An end effector assembly of a tissue resection device can comprise a first cut guide having a first distal peripheral portion; a second cut guide having a second distal peripheral portion, the second cut guide located around the first cut guide. Further, the first distal peripheral portion can be located distal of the second distal peripheral portion, and the first distal peripheral portion can be located farther laterally from a longitudinal axis of the end effector assembly than the second distal peripheral portion. The end effector assembly can further include a cutting device located between the first cut guide and the second cut guide, and the cutting device can be moveable relative to at least one of the first cut guide and the second cut guide.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 10 is a flow chart illustrating a method of performing a surgical procedure, in accordance with at least one example.

Figure 1:
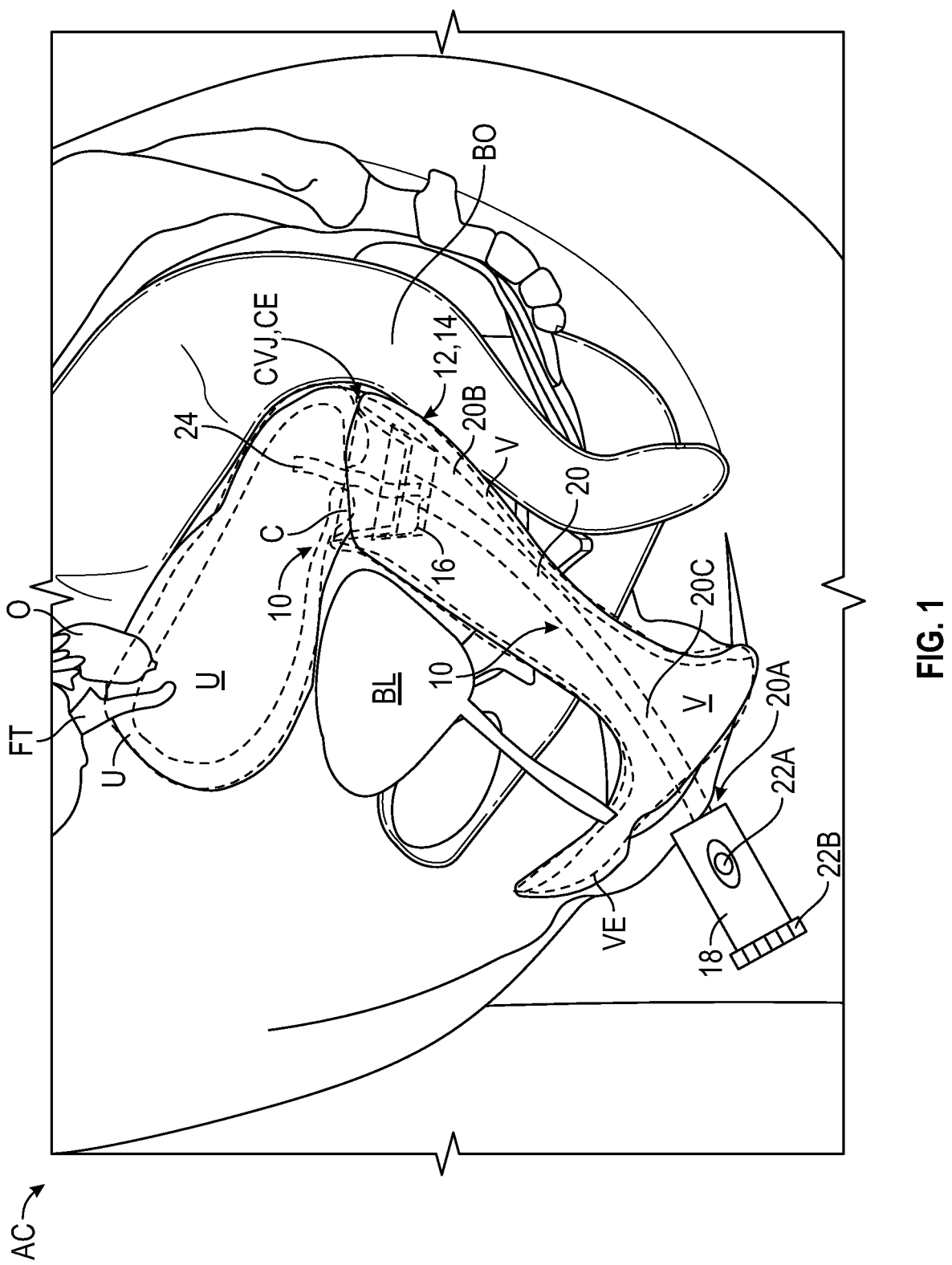
FIG. 1 is a schematic illustration of a medial view of female anatomy in an abdominal cavity including a portion of a medical instrument inserted into a vagina, in accordance with at least one example.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure provides systems and methods for performing a colpotomy procedure as part of a hysterectomy or other surgery. The present application is described with reference to performing female pelvic procedures, the systems and methods of the present disclosure can be used in other procedures, such as those that benefit from: delineating tissue for improved viewing by the surgeon; guiding a cutting device along a path; providing better visibility around a cutting device; or focusing energy into a tissue to be dissected while minimizing energy transfer to adjacent tissues. Further, the examples described in the present disclosure may also be used in the dissection and/or removal of other tissue or organs in both males and females.

Figure 2:
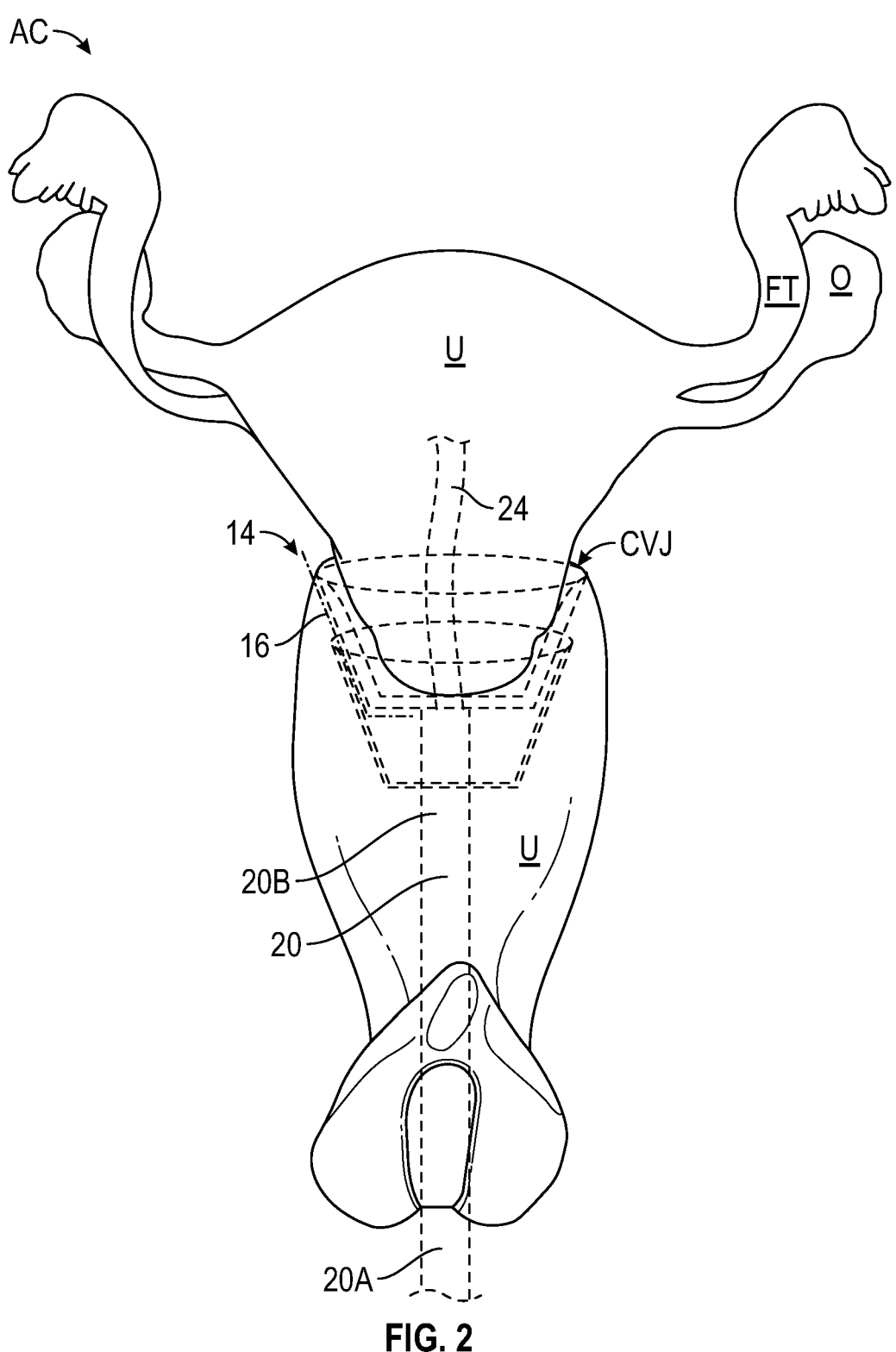
FIG. 2 is a schematic illustration of an anterior view of female anatomy in an abdominal cavity including a portion of the medical instrument of FIG. 1 inserted into the vagina, in accordance with at least one example.

FIG. 1 is a schematic illustration of a medial view of female anatomy in an abdominal cavity AC including a portion of a medical instrument 10 inserted into the vagina V of a patient. FIG. 2 is a schematic illustration of an anterior view of a portion of the female anatomy in an abdominal cavity AC shown in FIG. 1, including a portion of the medical instrument 10 of FIG. 1 inserted into the vagina V. FIGS. 1 and 2 are discussed concurrently.

To perform a colpotomy, a surgeon or other operator inserts a distal portion 12 of the medical instrument 10 including an end effector assembly 14 into a vulvar end VE of a patient's vagina V, guiding the end effector assembly 14 through the passageway of the vagina V, and seating the end effector assembly 14 proximate a cervical end CE of the vagina V as shown in FIGS. 1 and 2. With the end effector assembly 14 in place, the device operator can actuate a cutting device 16 to cut the vaginal tissue around the cervix C. In some procedures, the cutting device 16 can make a 360 degree cut in the vaginal wall VW to separate the cervix C and uterus U from the vagina V thereby facilitating resection of the uterus U and cervix C from the patient. For the purposes of this disclosure, "proximal" refers to the end of the device closer the device operator during use, and "distal" refers to the device end further from the device operator during use.

The medical instrument 10 can include a handle portion 18, an elongate member 20 and the end effector assembly 14. The handle portion 18 and elongate member 20 can aid a device operator in delivering the end effector assembly 14 to the cervical end CE of the vagina V. The handle portion 18 can be located at a proximal end portion 20A of the elongate member 20 and the end effector assembly 14 can be located at a distal end portion 20B of the elongate member 20. The elongate member 20 can include a body extending from the proximal portion to the distal portion and can include a lumen 20C extending therethrough. In the example, the handle portion 18 or the elongate member 20 can include one or more operator controls 22A, 22B to actuate the end effector assembly 14, such as to operate the cutting device 16. In some examples, the handle portion 18 and the one or more operator controls 22A, 22B can be omitted, modified or located elsewhere, such as to permit the use and operation of the medical instrument 10 in robotic surgery, or in a procedure actuated remotely or partially remotely. The handle portion 18 is shown to illustrate one possible example. A movable manipulator 24 of end effector assembly 14 can be inserted through the cervix C and into the uterus U to allow a surgeon to move the uterus U around during surgery to provide access to locations to be resected.

Figure 3:
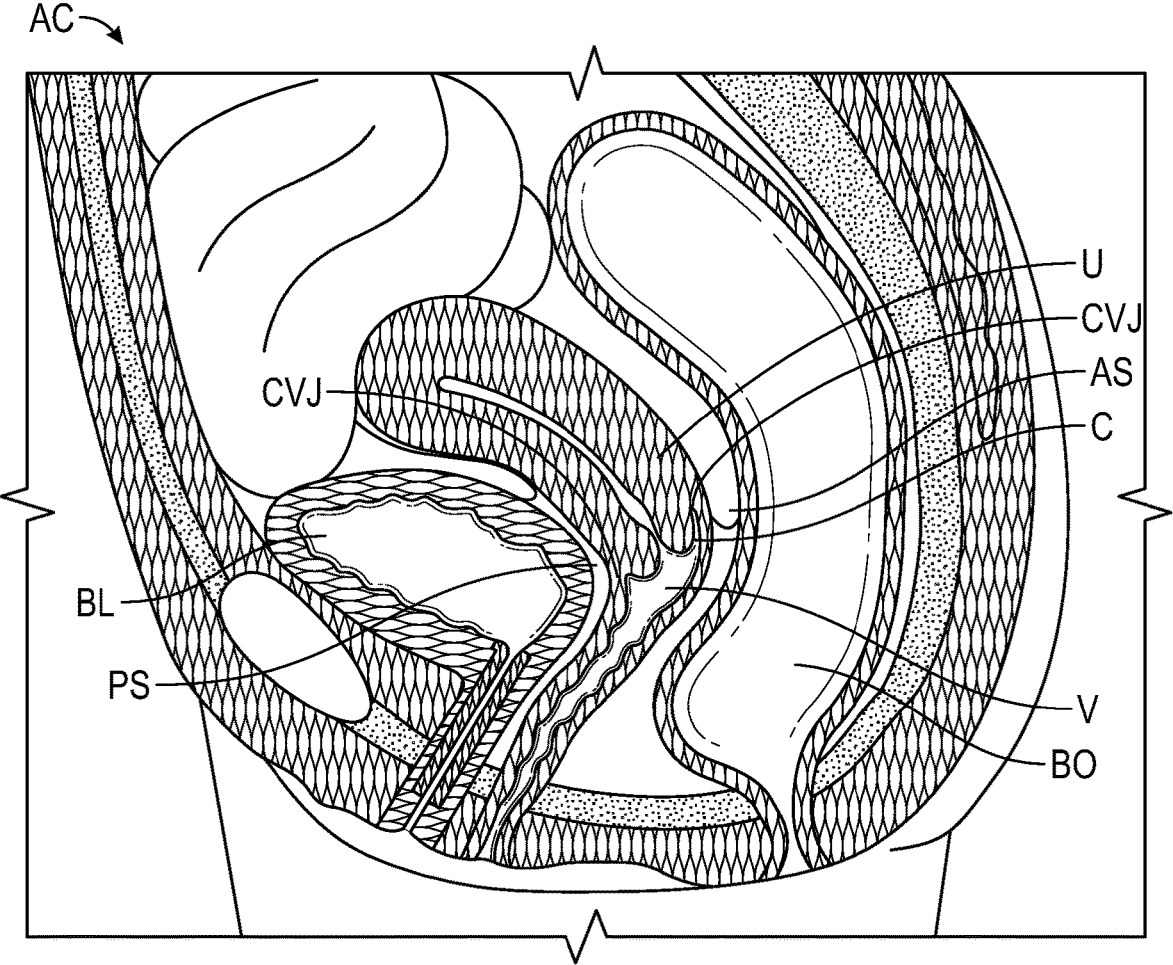
FIG. 3 is a schematic illustration of female anatomy in an abdominal cavity taken along a sagittal plane.

FIG. 3 is a schematic illustration of female anatomy in an abdominal cavity AC (e.g., pelvic anatomy) taken along a sagittal plane, without a medical instrument inserted into the vagina V. Normal female pelvic anatomy includes, among other things, a uterus U, a cervix C, vagina V, bladder BL and bowel BO. One of the challenges with performing a colpotomy is the proximity of the cervical-vaginal junction CVJ to other organs. A cutting device (such as cutting device 10 in FIGS. 1 and 2) can improve safety by limiting trauma to nearby tissue.

Figure 4A:
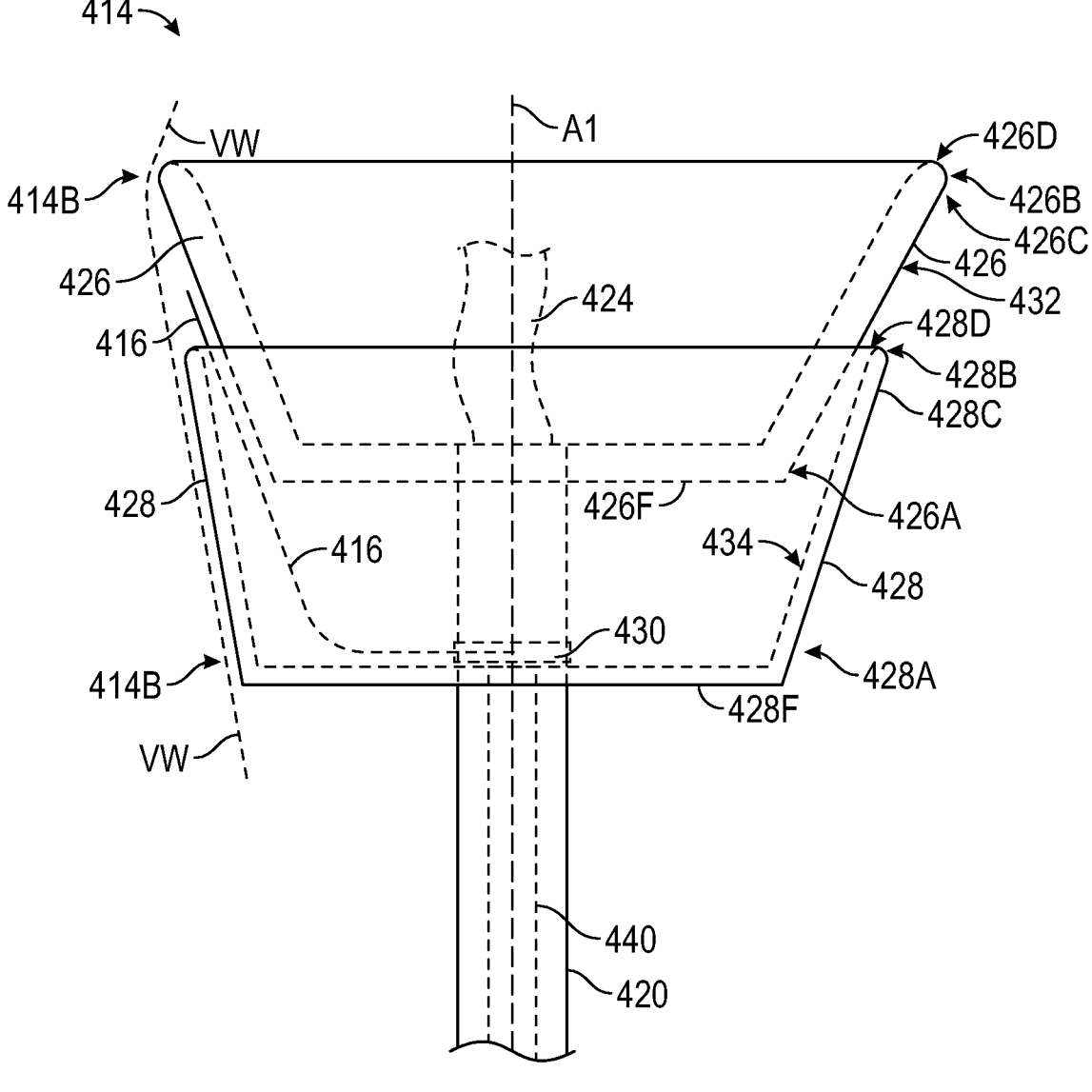
FIG. 4A is a schematic illustration of a side view of an example of an end effector assembly that can be used with the medical instrument of FIG. 1, with a cutting device in a retracted position, in accordance with at least one example.
Figure 4B:
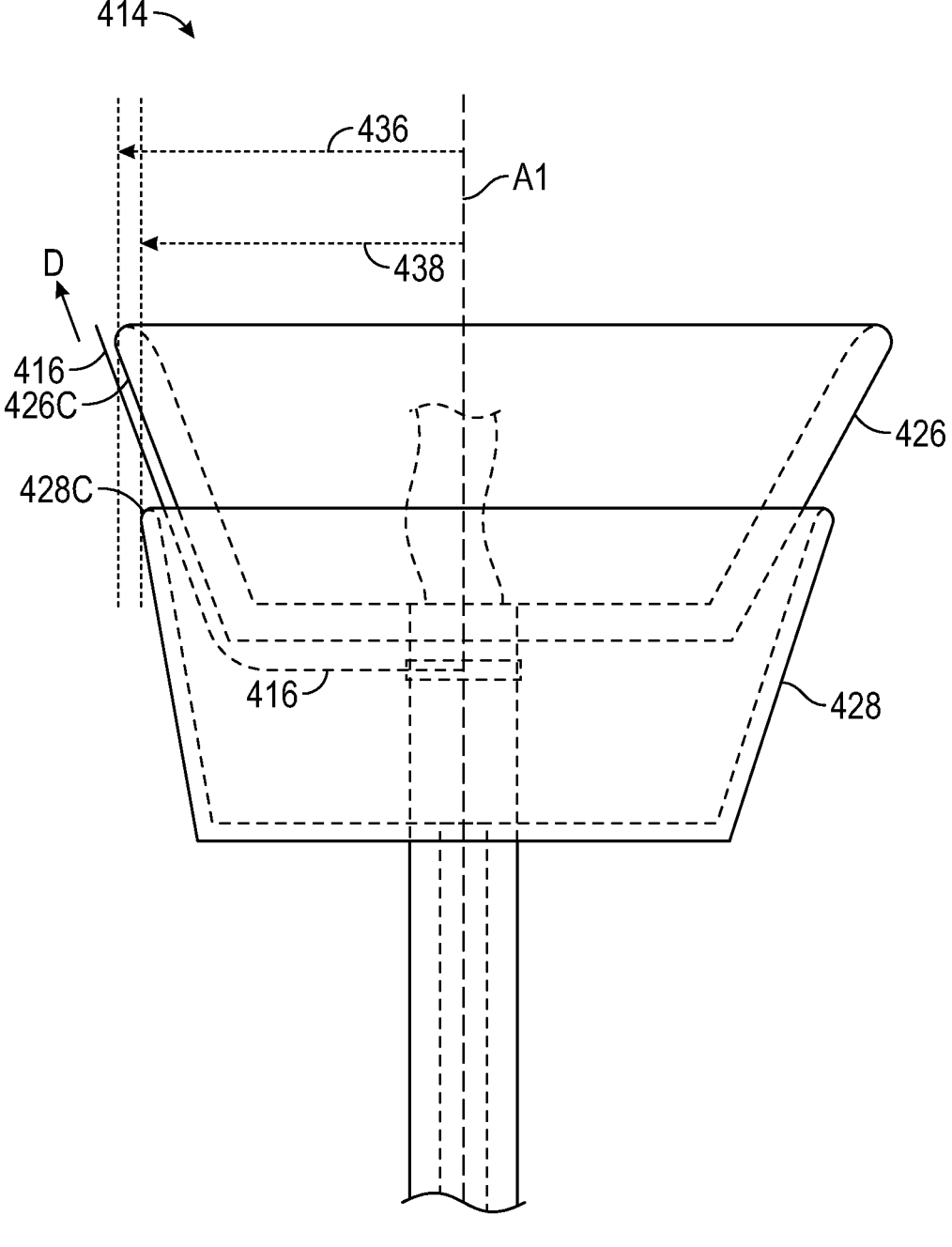
FIG. 4B is a schematic illustration of a side view of the end effector assembly of FIG. 4A with the cutting device in a deployed position, in accordance with at least one example.
Figure 4C:
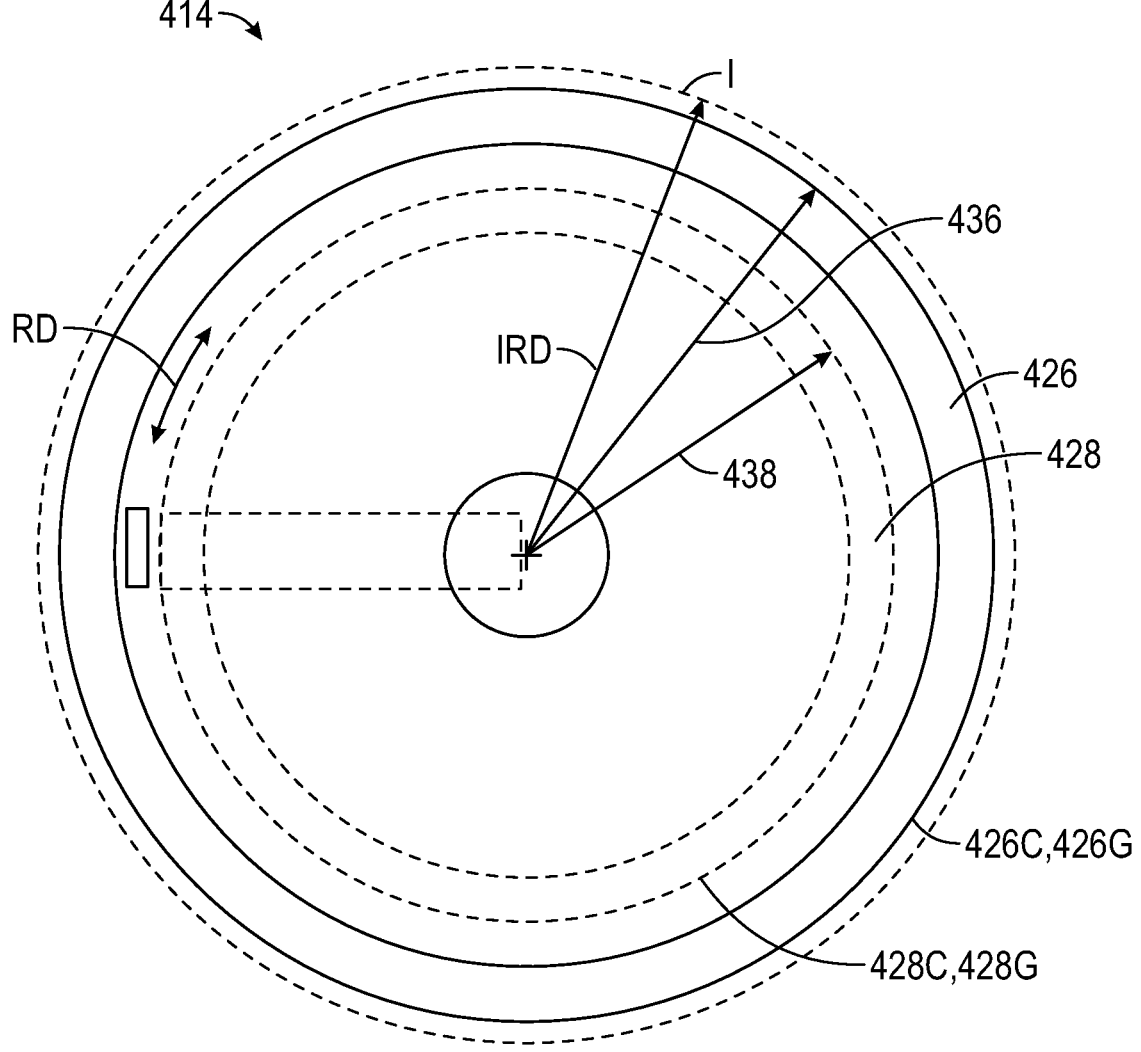
FIG. 4C is a schematic illustration of a top view of the end effector assembly of FIG. 4A, in accordance with at least one example.

FIG. 4A is a schematic illustration of a side view of an example of an end effector assembly 414 that can be used with the medical instrument 10 of FIG. 1, with a cutting device 416 in a retracted position. FIG. 4A also shows an example outline of a portion of a vaginal wall VW during insertion. FIG. 4B is a schematic illustration of a side view of the end effector assembly 414 of FIG. 4A with the cutting device 416 in a deployed position. FIG. 4C is a schematic illustration of a top view of the end effector assembly 414 of FIG. 4A. FIGS. 4A, 4B and 4C are discussed concurrently.

The end effector assembly 414 can extend along a longitudinal axis A1 from a proximal end 414A to a distal end 414B. The end effector assembly 414 can include a first cut guide 426, a second cut guide 428, a cutting device 416 located between the first cut guide 426 and the second cut guide 428, and a cutting device actuator 430 configured to deploy/actuate the cutting device 416. The end effector assembly 414 can also include a manipulator 424 that is insertable into a cervix C (FIG. 1) and movable to allow a surgeon to manipulate or move the uterus U during a surgical procedure.

The first cut guide 426 can include a first support surface 432 that extends from a first proximal end portion 426A to a first distal end portion 426B along a longitudinal axis A1 of the end effector assembly 414. In some examples, the first support surface 432 can be described as a first outer support surface that faces outward, away from the longitudinal axis A1. The first distal end portion 426B can include a first outer distal portion 426C at an outer distal surface.

The first support surface 432 can extend along a longitudinal axis A1 of the end effector 414, however, the first support surface 432 does not need to be parallel or coaxial to the longitudinal axis A1. For example, the description of the first support surface 432 extending along the longitudinal axis A1 can describe a reference to the general longitudinal direction that the first support surface 432 extends along the longitudinal axis A1. For example, the first support surface 432 can extend along the longitudinal axis A1 in a non-parallel manner as shown in FIG. 4A. In some examples, the first support surface 432 may be described as tapered, angled, fluted, or the like.

The second cut guide 428 can include any of the features described with respect to the first cut guide 426, and therefore all features may not be described in further detail. The second cut guide 428 can be located around the first cut guide 426. The second cut guide 428 can include a second support surface 434 that extends from a second proximal end portion 428A portion to a second distal end portion 428B. In some examples, the second support surface 434 can be described as a second inner support surface that faces inward towards the longitudinal axis A1 or faces the first support surface 432 (e.g., outer support surface) of the first cut guide 426. The second distal end portion 428B can include a second outer distal portion 428C at an outer distal surface. In some examples, the second support surface 434 may be described as tapered, angled, fluted, or the like.

As shown in FIG. 4A, the first outer distal portion 426C and the second outer distal 428C portion can be spaced apart in a direction along the longitudinal axis A1. For example, the first outer distal portion 426C can be located distal of the second outer distal portion 428C. In some examples, the first outer distal portion 426C and the second outer distal portion 428C can be described as the outermost portions farthest from the longitudinal axis A1. The first outer distal portion 426C and the second outer distal portion 428C may be located at first and second distal terminating ends 426D, 428D. However, in some examples, and as shown in the example of FIG. 4A, the first outer distal portion 426C and the second outer distal portion 428C can be located slightly proximal of the first and second terminating ends 426D, 428D in the first and second distal end portions 426B, 428B such as when the first and second distal portions 426A, 426B are rounded.

When the end effector assembly 414 is inserted into the vagina (V, FIG. 1) of the patient, the second outer distal portion 428C can be configured to follow the first outer distal portion 426C. As shown in FIG. 4B, the first outer distal portion 426C can be located farther laterally from the longitudinal axis A1 than the second outer distal portion 428C. In this arrangement, the first outer distal portion 426C is configured to displace a vaginal wall (VW, FIG. 1) of the patient to a first dimension (e.g., 436) and the second outer distal portion 428C is configured to displace the vaginal wall VW of the patient to a second dimension (e.g., 438). The first dimension can be greater than the second dimension.

Explained another way, the first outer distal portion 426C can be located a first radial distance 436 away from the longitudinal axis A1, and the second outer distal portion 428C can be located a second radial distance away 438 from the longitudinal axis A1, and further, the first radial distance 436 can be greater than the second radial distance 438. In some examples, the first and second cut guides 426, 428 can be frustoconical, or include sections having a circular cross-section in a direction perpendicular to the longitudinal axis A1. The radial distances can define radii of one or more of the first and second cut guides 426, 428. However, the first and second cut guides 426, 428 need not necessarily be frustoconical in all examples. Here, describing a radial direction can be directional description and does not require that the first and second cut guides 426, 428 have circular cross-sections in a direction perpendicular to axis A1.

In the example of FIGS. 4A, 4B and 4C, the first and second cut guides 426, 428 are shown as cup-shaped guides. The first and second cut guides 426, 428 can take on other forms such as partial cups, rings, partial rings or irregular shapes. In the illustrative example, the first cut guide 426 can be cup-shaped and include a substantially frustoconical shape that tapers down from the first distal end portion 426B to the first proximal end portion 426A and having a first base 426F. Likewise, the second cut guide 428 can be cup-shaped and can include a substantially conical shape that tapers down from a second distal end portion 428B to a second proximal end portion 428A having a second base 428F. In other words, the first cut guide 426 can form an inner cup portion positioned within the second cut guide 428 which forms an outer cup portion. At least one of the inner cup portion (e.g., 426) and the outer cup portion (e.g., 428) can guide the cutting device 416. In some examples, both the inner cup portion and the outer cup portion guide the cutting device 416.

As shown in FIG. 4C, the first outer distal portion 426C can form a first distal peripheral portion 426G, and the second outer distal portion 428C can form a second distal peripheral portion 428G. The first distal peripheral portion 426G can include a continuous surface around the first cut guide 426 at the first outer distal portion 426C. Likewise, the second distal peripheral portion 428G can form a continuous surface around the second cut guide 428 at the second outer distal portion 428C. In some examples, the first distal peripheral portion 426G or the second distal peripheral portion 428G can be frustoconical or have a circular, oval, elliptical or irregular cross-section. In some examples the first distal peripheral portion 426G or the second distal peripheral portion 428G may be discontinuous, such as, but not limited to, when a procedure does not require a 360 degree cut.

The first distal peripheral portion 426G of the first cut guide 426 can be configured to displace a vaginal wall (VW; FIG. 4A, FIG. 1) of a patient to a first dimension (e.g., 436, FIG. 4B) when inserted into a vagina of the patient, and the second distal peripheral 428G portion of the second cut guide 428 can be configured to displace a vaginal wall VW of the patient to a second dimension. (e.g., 438, FIG. 4B). The first dimension can be greater than the second dimension. In such an example, the first dimension can be approximately equal to the first radial distance 436 and the second dimension can be approximately equal to the second radial distance 438 (FIGS. 4B, 4C).

Explained in further detail, one of the benefits of the example end effector assembly 414 of FIGS. 4A, 4B and 4C over conventional end effector assemblies is that the end effector assembly 414 may be more easily inserted into the textured, curved and generally torturous path of the vagina (V, FIG. 1). When inserted into a vagina, the second cut guide 428 follows the first cut guide 426. Because the first cut guide 426 has can include the first distal peripheral portion 426G being larger than the second distal peripheral portion 428G of the second cut guide 428, the first cut guide 426 can displace the vaginal wall VW during insertion, while the second cut guide 428, which does not extend as far laterally, can follow along in the "shadow" or "path" of the first cut guide 426 without further displacing the vaginal wall or displacing the vaginal wall less than the displace-ment caused by the first cut guide 426. The end effector assembly 414 may be easier to insert compared to a device where a second cut guide has a larger periphery (e.g., perimeter, footprint) than a first cut guide.

With continued reference to FIGS. 4A, 4B and 4C, the cutting device 416 can be located between the first cut guide 426 and the second cut guide 428. The cutting device 416 can be deployed by the cutting device actuator 430 that is operably coupled to operator controls (22A, 22B; FIG. 1). The cutting device actuator 430 can be configured to actuate movement of the cutting device 416 to cause at least portion of the cutting device 416 to protrude beyond the first outer distal portion 426C and the second outer distal portion 428C.

For example, the cutting device 416 can be configured to move relative to distal end between a retracted position shown in FIG. 4A and a deployed position shown in FIG. 4B, such as along the direction shown by deployment arrow. In some examples, when retracted, the cutting device 416 may not extend laterally or radially beyond the first outer distal portion 426C, Further, in some examples, the cutting device 416 may not extend laterally or radially beyond the second outer distal portion 428C. When deployed, the cutting device 416 can move in a direction having a longi-tudinal component and a lateral component.

In addition to be deployed and retracted, the cutting device 416 can also be configured to be rotated about the longitudinal axis A1 to move the cutting device 416 relative to one or more of the first cut guide 426 and the second cut guide 428 in the direction shown by rotation direction RD in FIG. 4C. In some examples, the operator can rotate the cutting device 416 approximately 360 degrees about the longitudinal axis to make an incision I through the vaginal wall (also see VW, FIG. 1) around the cervix, thereby separating the cervix and uterus from the vagina. In some examples, the incision I is a generally circular-shaped inci-sion, but can be any suitable shape such as an oval shape or irregular shape, and need not be a full 360 degree cut or a continuous 360 degree cut.

The cutting device 416 can be operably coupled to any suitable cutting device actuator 430 to deploy and rotate the cutting device 416. The cutting device actuator 430 can be operated by, for example, one or more user controls (22A, 22B; FIG. 1) located proximal to the cutting device 416, such as on the elongate member 420 or the handle portion (e.g., 18, FIG. 1). The cutting device actuator 430 can be located in any suitable location on the medical instrument (e.g., 10, FIG. 1) to facilitate actuation of the cutting device 416, such as located at one or more of: the end effector assembly 414, the elongate member 420 and the handle portion 18.

For example, movement between the deployed and retracted positions may be accomplished via the first user control 22A (FIG. 1) including a first actuating mechanism such as a slide actuator that can be operably coupled to the cutting device 416. The first actuating mechanism can be any actuating mechanism known to one skilled in the art for deploying a cutting device.

Rotational movement can be accomplished via a second user control 22B (FIG. 1) including a second actuating mechanism, such as a rotational actuator. In one example, the second actuation mechanism can facilitate rotation of a rod 440 within the elongate member 420 while the rod 440 is coupled to the cutting device 416. The second actuating mechanism can be any actuating mechanism known to one skilled in the art for controlling rotation of the cutting device 416.

With reference to the combination of FIGS. 1, 2 and FIGS. 4A-4C, the inventor discovered that it may be desirable to create an incision I (FIG. 4C) in the vaginal tissue at a location in the vaginal wall VW (FIG. 1) that is "offset" or located farther laterally from the longitudinal axis A1 than the lateral position of the first outer distal end 428C. The combination of the first and second cut guide 426, 428 geometries and the deployment direction of the cutting device 416 contribute to solving this problem, because the cutting device 416 can be deployed to extend laterally and longitudinally beyond the first outer distal portion 426C and the second outer distal portion 428C, as shown in FIG. 4B. Thus, the cutting device 416 is deployable in a direction D having both a longitudinal component and a lateral component. Therefore, the incision radial distance IRD from the longitudinal axis A1 of the end effector assembly 414 can be larger than the first radial distance 436 or the second radial distance 438. As shown in FIG. 4C, the result of this arrangement is that when the cutting device 416 is rotated about the longitudinal axis A1 along rotation direction RD, the incision path can result in an incision periphery I that is the same as or larger than the peripheries of the first outer distal portion 426C of the first cut guide 426 or the second outer distal portion 428C of the second cut guide 428. In some examples, the incision radial distance IRD may be in a range between 1-30% greater than the first radial distance 436. In a possibly more preferred example, the incision radial distance IRD may be in a range between 0.5-10% greater than the first radial distance 436. One of the benefits is that this allows for smaller cut guides to perform larger incisions than has been achieved with conventional devices.

The cutting device 416 can be any known cutting device, including, but not limited to, any one or more of a sharpened blade, cautery blade, radio-frequency scissors, microwave probe, or ultrasonic ablation device. In some examples, the cutting device 416 can be an electrosurgical device connected through an electrical line to an energy source, such as, for example, an RF generator. The cutting device 416 can be a monopolar type device. The cutting device 416 can be used in a system including a grounding pad for placement under the patient.

Figure 5:
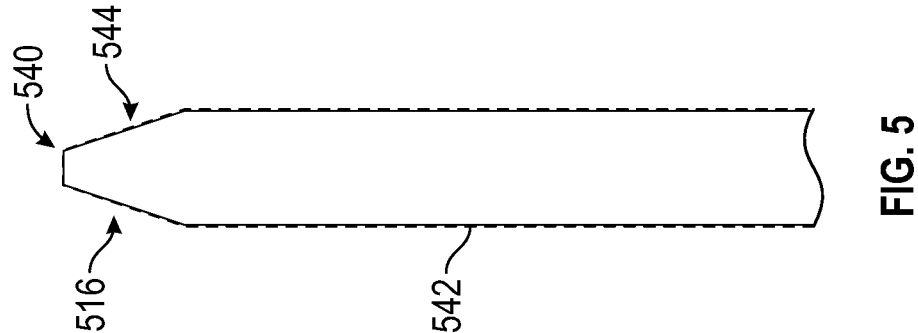
FIG. 5 is a schematic illustration of a planar view of a first example of a cutting device that can be used with the end effector of FIGS. 4A-4C, in accordance with at least one example.

FIG. 5 is a schematic illustration of a planar view of a first example of a cutting device 516 that can be used with the medical instrument 10 and end effector assemblies 14, 414 of FIGS. 4A-4C. While the cutting devices described herein can be used with the end effector assemblies 14, 414, any of the cutting devices can be used with other medical instruments and end effector assemblies. Likewise, other cutting devices can also be used with the medical instruments 10 and end effector assemblies 14, 414 described herein.

The cutting device 516 can include a sharpened portion 540 along at least a portion of a perimeter 542. A tip portion 544 of the cutting device 516 can be configured to puncture a tissue, such as tissue proximate a cervical-vaginal junction CVJ of a patient during a colpotomy procedure as described with reference to FIGS. 1 and 2. All or a portion of the cutting device 516 can be formed of one or more materials including an optically transparent material. The optically transparent material can be optically transparent to a light source provided, such as an infrared (IR) light source, or light from any given wavelength, including, but not limited to, visible light including blue light. In some examples, optically transparent can be defined as mostly optically transparent or more than 50% transparent to an incident beam of light therethrough. In some examples, the optical transparency can be in a range between 30-100% transparent to an incident beam of light therethrough.

The inventor has discovered that an optically transparent cutting device can provide not only the strength and sharpness needed to resect tissue. The optically transparent material can also provide improved visibility at a surgical site. The optically transparent material allows the passage of light through the cutting device 516. In some examples, the optically transparent material is also an insulative-type material that is resistant or mostly resistant to conducting electricity.

Suitable materials for the cutting device 516 can include, but is not limited to, ceramics including advanced industrial materials that are developed for use in optical applications. In some examples, suitable optically transparent materials can include anything that is transmits at least 30% of electromagnetic radiation in the spectral range between 250-2000 nm. Suitable examples of optically transparent materials can include, but is not limited to, alumina, zirconia, zirconia doped with other metal oxides, glass or any other ceramic. In some examples, polymer materials can also be used.

Figure 6B:
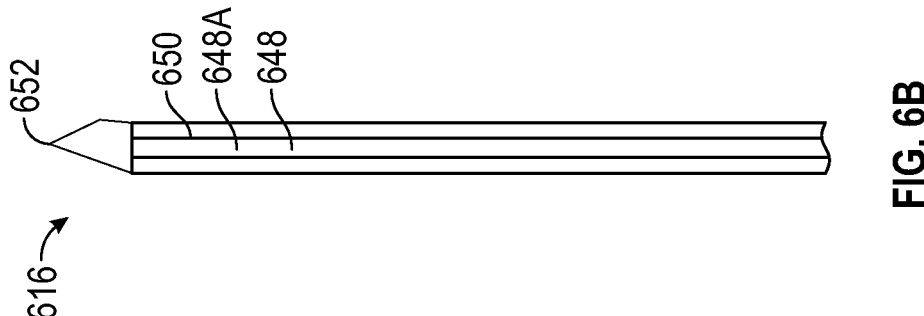
FIG. 6B is schematic illustration of a side view of the second example of a cutting device of FIG. 6A, in accordance with at least one example.
Figure 6A:
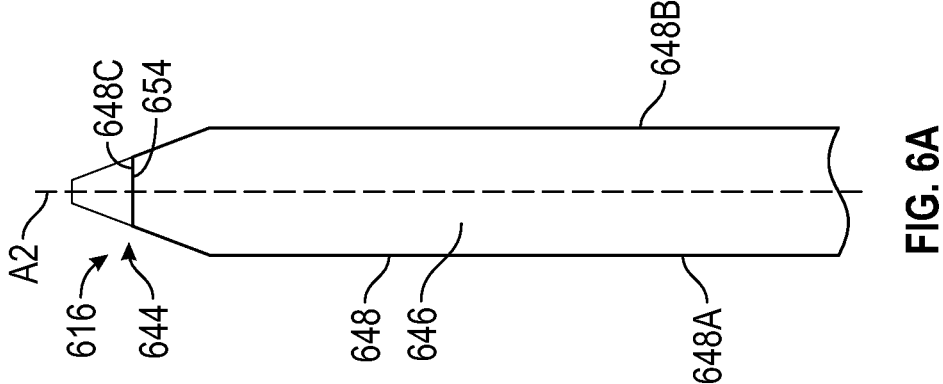
FIG. 6A is schematic illustration of a planar view of a second example of a cutting device that can be used with the end effector of FIGS. 4A-4C, in accordance with at least one example.

FIG. 6A is schematic illustration of a planar view of a second example of a cutting device 616 that can be used with the end effectors 14, 414 of FIGS. 1, 2 and 4A-4C. FIG. 6B is schematic illustration of a side view of the second example of a cutting device 616 of FIG. 6A. Any of the features described in the FIGS. 1, 2, 4A, 4B and 5 can be used with the example cutting device 616 of FIGS. 6A and 6B. FIGS. 6A and 6B are described concurrently.

As shown in FIG. 6A, the cutting device 616 can include a central portion 646 and a peripheral portion 648, such as an insulative central portion 646 at least partially surrounded by a conductive peripheral portion 648. The insulative central portion 646 can be electrically-insulative to block or limit the flow of electrical current therethrough. The conductive peripheral portion 648 can be electrically-conductive to permit the flow of electrical current therethrough. In some examples, the insulative central portion 646 is electrically less conductive than the conductive peripheral portion 648 such that the majority of the current travels through the conductive peripheral portion 648. A benefit of the conductive peripheral portion 648 at least partially surrounding the insulative central portion 646 is that the electrical flow can be administered to the tissue to be cut in a highly focused way. Because the energy can be applied through the electrically-conductive peripheral portion 648, this helps to focus the energy being delivered to the tissue to be cut, while reducing energy applied to the surrounding tissue that is not being cut, reducing the thermal spread into tissues adjacent to a cut location. In particular, a higher current density can be delivered through the electrically-conductive peripheral portion 648 when the central portion 646 is electrically-insulative, than if the central portion 646 was also electrically-conductive.

The insulative central portion 646 can extend along a longitudinal path LP, which in some examples, may be a longitudinal axis A2. The conductive peripheral portion 648 can include at least one of a first lateral conductive portion 648A and a second lateral conductive portion 648B separated by the insulative central portion 646. In some examples the first lateral conductive portion 648A and the second lateral conductive portion 648B are in electrical communication with each other, such as via a transverse conductive portion 648C proximate, passing through, or passing adjacent to a tip portion 644 of the cutting device 616.

The insulative central portion 646 can include an optically transparent material such as those described with respect to FIG. 5. The conductive peripheral portion 648 can include a metal material such as a metal wire or metal string coupled to the insulative central portion 646. In some examples, the conductive peripheral portion 648 can be positioned in a channel 650 of the insulative central portion 646, as shown in FIG. 6B. The channel 650 can include a recess in the insulative central portion 646.

In some examples, the cutting device 616 can be an electrosurgical device with the conductive peripheral portion 648 being configured to be coupled through an electrical line to an energy source, such as, for example, an RF generator. The conductive peripheral portion 648 can be coupled to the energy source by any suitable means known in the art.

In some examples, the cutting device 616 can include the tip portion 644, such that at least portion of the tip portion extends distal of the conductive peripheral portion 648. The tip portion 644 can include an optically transparent or mostly transparent material such as those described with respect to FIG. 5. The tip portion 644 can provide a sharp edge 652 configured to pierce through tissue such a cervical-vaginal junction (CVJ, FIGS. 1 and 2). For example, the tip portion 644 can include the sharp edge 652 having a sharpness configured to perform a colpotomy. In other examples, the portion of the tip portion 644 that extends distally of the conductive peripheral portion 648 can be omitted and the conductive peripheral portion 648 can surround an entirety of the insulative central portion 646.

In some examples, the first lateral conductive portion 648A and the second lateral conductive portion 648B can be in electrical communication with each other and with the tip portion 644 via a conductive tip portion. The conductive tip portion (e.g., 644) can be conductive, mostly conductive, or partially conductive.

Figure 7:
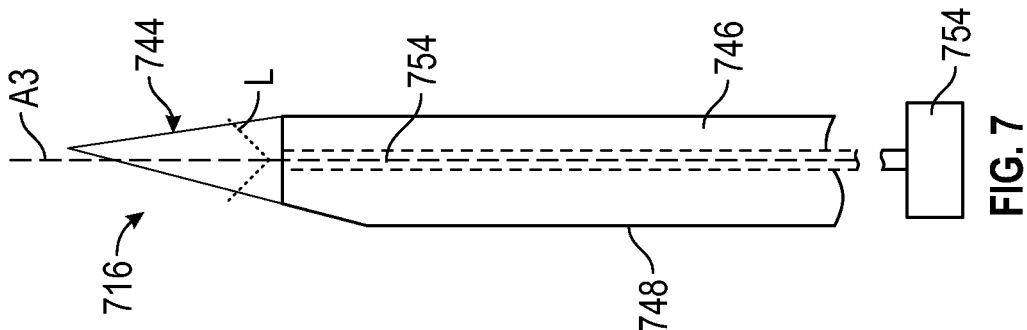
FIG. 7 is a schematic illustration of a side view of a third example of a cutting device that can be used with the end effector of FIGS. 4A-4C, in accordance with at least one example.

FIG. 7 is a schematic illustration of a side view of a third example of a cutting device 716 that can be used with the end effectors 14, 414 of FIGS. 1, 2 and 4A-4C. Any of the features described in the examples of FIGS. 1, 2, 4A, 4B, 5, 6A and 6B can be used with the example of FIG. 7, including, but not limited to, features of the optically transparent and/or insulative central portions 746, conductive peripheral portions 748 or tip portion 744.

As shown in FIG. 7, the cutting device 716 can extend along a longitudinal path and can include an optical pathway 754 configured to carry light received from a proximal light source 756 to an optically transparent tip portion 744 of the cutting device 716. Some of the benefits of the optical pathway 754 is improved visibility of the vagina and cervix within the vagina of the patient. Additionally, a surgeon accessing the other side of the tissue as during a laparoscopic surgery can see at least a portion of the light from the light source 756 passing through the tissue. The transmission of light from the proximal light source 756 to the tip portion 744 of the cutting device 716 and through the tissue can thereby act as a guide for the surgeon and can help to orient the surgeon to the location of the cutting device 716 or colpotomy cup on the other side of the tissue to be cut. While the benefits of the cutting device 716 including an optical pathway 754 are described with respect to use with a colpotomy cup, the features of the cutting device 716 are not thereby limited and can be used in other surgical procedures.

The optical pathway 754 can extend through the insulative central portion 746, such as through a lumen located within the insulative central portion 746 or a recess in the insulative central portion 746. In some examples, at least a portion of the optical pathway 754 may not be completely recessed or fully flush with the insulative central portion 746 and only a portion of the optical pathway 754 is located within the insulative central portion 746.

The optical pathway 754 can extend along the longitudinal path of the cutting device 716. In some examples, the longitudinal path A3 of the cutting device 716 can be defined as a longitudinal axis A3 of the cutting device 716, but in other examples, the longitudinal path is not necessarily limited as such. In some examples, the longitudinal path does not need to be straight and the cutting device 716 does not need to be straight.

In some examples, the cutting device 716 can include a conductive peripheral portion 748, such as the conductive peripheral portions 648 of FIGS. 6A and 6B.

Figure 8B:
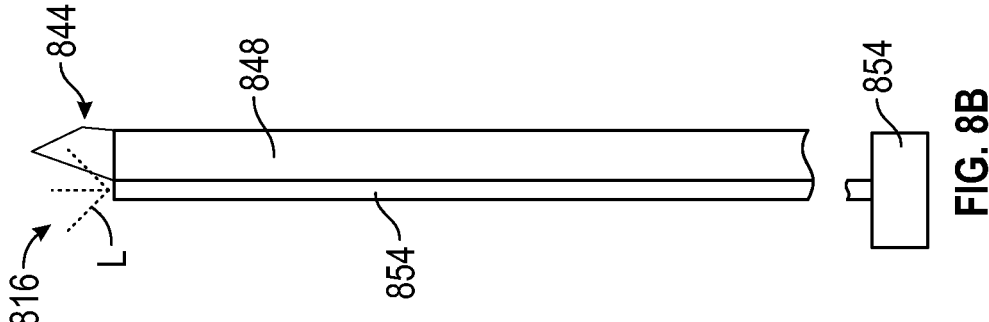
FIG. 8B is a schematic illustration of a side view of the fourth example of a cutting device of FIG. 8A, in accordance with at least one example.
Figure 8A:
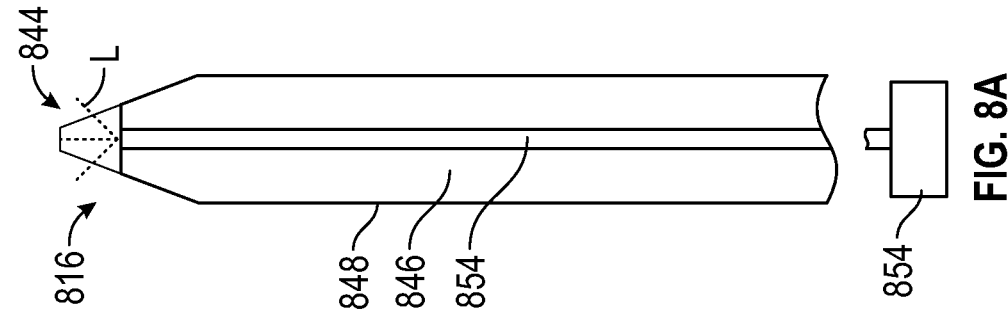
FIG. 8A is a schematic illustration of a planar view of a fourth example of a cutting device that can be used in the end effector of FIGS. 4A-4C, in accordance with at least one example.

FIG. 8A is a schematic illustration of a planar view of a fourth example of a cutting device 816 that can be used with the end effectors 14, 414 of FIGS. 1, 2 and 4A-4C. FIG. 8B is a schematic illustration of a side view of the fourth example of a cutting device 816 of FIG. 8A. Any of the features described in the examples of FIGS. 1, 2, 4A, 4B, 5, 6A, 6B and 7 can be used with the example of FIGS. 8A and 8B. FIGS. 8A and 8B are described concurrently.

The example cutting device 816 in FIGS. 8A and 8B can share similarities with the cutting device 716 of FIG. 7, and therefore all features may not be described in further detail. For example, FIGS. 8A and 8B can include a cutting device 816 having a central portion 846 and an optical pathway 854. In some, but not all examples, the illustrative central portion 846 can be insulative and at least partially surrounded (e.g., bordered) by a conductive peripheral portion 848 as described in other examples. FIGS. 8A and 8B can include any of the features of the optical pathway 754 of FIG. 7.

In addition, in FIG. 8B, the optical pathway 854 configured to carry light L received from a proximally located light source 856 to a distal end of the cutting device 816, such as an optically transparent tip portion 844 of the cutting device 816, can be located adjacent to the central portion 846 instead of through the central portion 846. The optical pathway 854 can deliver light L to a distal end of the cutting device 816, such as to an optically transparent tip portion 844. In some examples, the optically transparent tip portion 844 can be configured to receive light L from the proximally located light source 856 and disperse the light L through the distal end of the cutting device 816.

Figure 9:
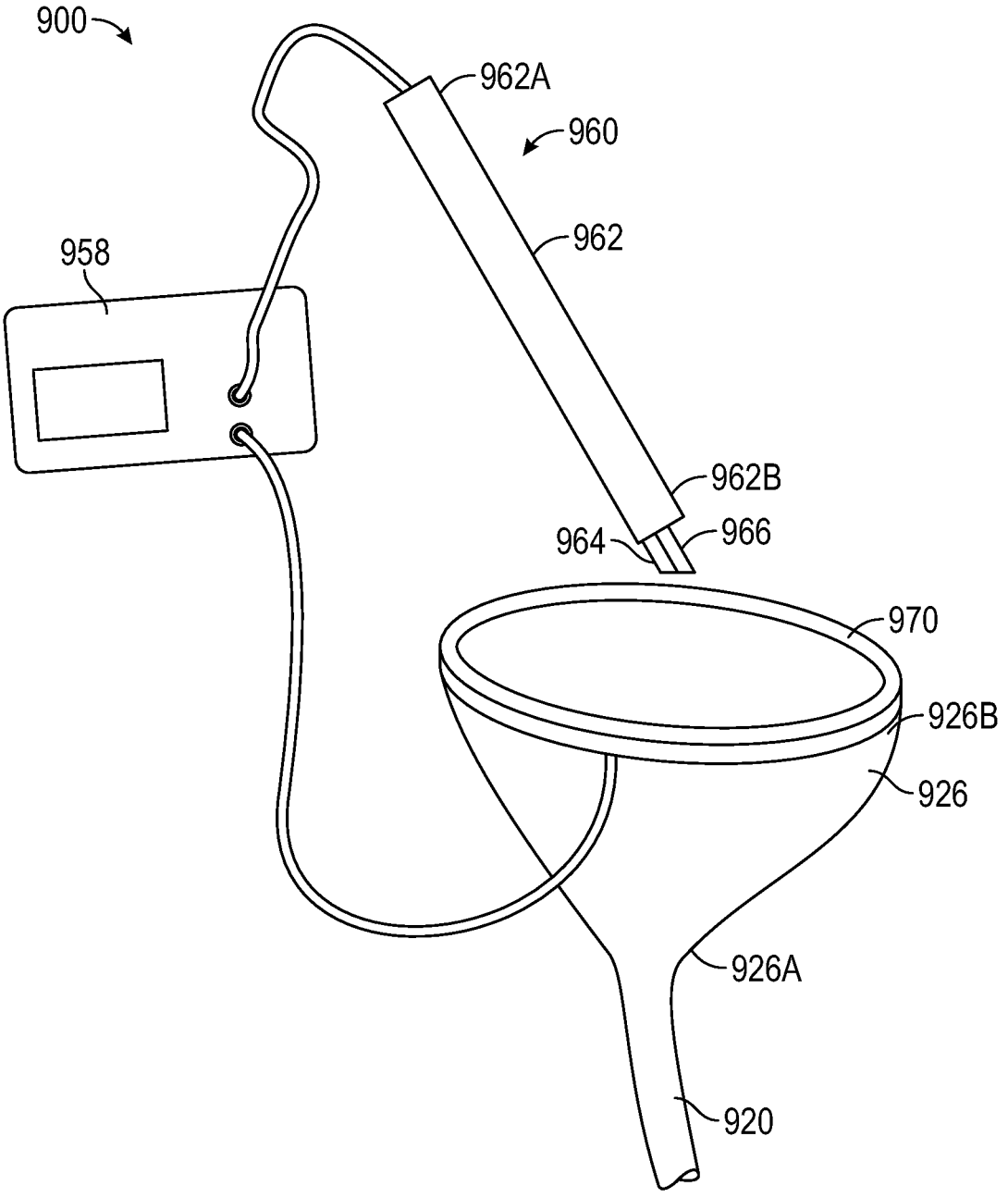
FIG. 9 is a schematic illustration of an isometric view of a surgical system including an electrosurgical generator assembly and an end effector assembly, in accordance with at least one example.

FIG. 9 is a schematic illustration of an isometric view of a surgical system 900 including an electrosurgical generator 958. The surgical system 900 of FIG. 9 can incorporate any of the features illustrated in the examples of FIGS. 1, 2, 4A-4C, 5, 6A, 6B, 7, 8A and 8B. The surgical system 900 is described with reference to and can be used to perform a colpotomy procedure, however, aspects of the surgical system 900 can be used to perform other procedures.

The surgical system 900 can include a medical instrument system 910 having a tissue resection device 960 and a cut guide 926. In the illustrative example of FIG. 9, the cut guide 926 is shown as a colpotomy guide configured to be inserted into a vulvar end VE of a vagina V of a patient and be seated proximate a cervical-vaginal CVJ junction of the patient (see FIGS. 1 and 2). The cut guide 926 can be located at a distal end of an elongate member 920 and can extend from a proximal end portion 926A to a distal end portion 926B. The distal end portion 926B of the cut guide 926 can include a magnet-attracting portion 970. As shown in illustrative example of FIG. 9, the magnet-attracting portion 970 can be provided as a conductive rim (e.g., ring, metal ring. The magnet-attracting portion 970 can include a material that magnets are attracted to, including ferromagnetic metals such as iron, nickel and cobalt. The magnet-attracting portion 970 can be configured to be electrically couplable to the electrosurgical generator 958. Although the magnet-attracting portion 970 is located at a distal end portion 926B of the cut guide 926, in other examples, the magnet-attracting portion 970 can be located elsewhere on the cut guide 926, or at another location on a different guide having a different shape or different cut shape to be performed.

The surgical system 900 can also include a tissue resection device 960 (e.g., tissue resection instrument) that is configured to be coupled to the electrosurgical generator 958. The tissue resection device 960 can include a body 962 manipulatable by a user, a magnet 964 and an electrode 966. The body 962 can be moved by a user (e.g., or a robot) to facilitate delivery of the magnet 964 and the electrode 966 to a tissue to be resected, such as, but not limited to, a cervical-vaginal junction (CVJ, FIGS. 1, 2). The magnet 964 can be described as a magnetic locator and can be formed of any suitable magnetic material. The body 962 can extend from a proximal portion 962A to a distal portion 962B. The distal portion 962B of the tissue resection device 960 can include the magnet 964 and the electrode 966. In the illustrative example of FIG. 9, the magnet 964 can be configured to be attracted to the magnet-attracting portion 970 of the cut guide 926 when a tissue such as a cervical-vaginal junction of a patient is positioned between the magnet and the magnet-attracting portion 970. During resection, the magnet-attracting portion 970 of the cut guide 926 and the tissue resection device 960 can be positioned in contact with opposite sides of a patient's cervical-vaginal junction (e.g., CVJ, FIGS. 1, 2), or other tissue. The electrode 966 can be configured to transmit electrical energy to a tissue to be treated. In some examples the tissue resection device 960 can deliver the electrical energy to the tissue to treat the tissue, the remaining electrical energy is then received by the magnet-attracting portion 970 (e.g., conductive perimeter, conductive rim, metal ring) and sent back to the electrosurgical generator 958, completing the circuit. In some examples, the magnet-attracting portion 970 can be formed of a material that is both magnetic and electrically conductive (e.g., metal). In some examples, the magnet-attracting portion can include a plurality of materials to provide both magnet attracting characteristics and electrically conductive characteristics. In some examples both the magnet-attracting portion 970 and the magnet 964 can be magnets (e.g., both produce magnetic fields that attract each other).

The magnet 964 can be formed of any suitable magnet material(s), such as, but not limited to, magnets that are attracted to ferrous metals. The magnet-attracting portion 970 can be formed of any suitable material(s) such as, but not limited to, ferrous metals. In some examples, the magnet 964 can induce an attractive magnetic field when placed a distance in a range between 1 mm-1 cm of the magnet-attracting portion 970 with tissue such as vaginal tissue located therebetween. In some examples, the material properties of the magnet-attracting portion 970 and the magnet 964 can be reversed, such that the magnetic field is retained between the tissue resection device 962 and the cut guide 926.

For example, instead of the tissue resection device 960 including a magnet 964 and the cut guide 926 including a magnet-attraction portion 970, the tissue resection device 960 can include a magnet-attracting material (instead of or in addition to magnet 964), and the cut guide 926 can include a magnet (instead of or in addition to a magnet attracting material), such that an attractive magnetic field is created between the tissue resection device 960 and the cut guide 926 when the tissue resection device and the cut guide 926 are located on opposite sides of a tissue to be cut and in a position to perform a cut. In other words, any combination of materials, shapes, sizes and locations can be used such that the tissue resection device 960 and the cut guide 926 are configured to create a magnetic field between each other to provide guidance to an operator performing a cut or other treatment procedure.

The illustrative example of a surgical system 900 described with respect to performing a colpotomy procedure is provided merely for the purposes of illustration. In other examples for other procedures that resect tissue from a body or include cutting of tissue, especially in laparoscopic applications, the magnet 964 can be configured to be attracted to a different magnet-attracting portion of a different cut guide when a tissue to be resected is positioned between a magnet and a magnet attracting portion, such as to perform a different procedure, or resect a different tissue.

FIG. 10 is a flow chart illustrating a method 1000 of performing a surgical procedure, such as a tissue resection procedure, including but not limited to, a colpotomy procedure. The method 1000 can be performed using the surgical system 900 of FIG. 9. In some examples, aspects of any of the end effectors 14, 414 and aspects of any of the cutting devices 16, 416, 516, 716 and 816 can be used with the method 1000, but the method 1000 can also be used with other surgical systems. Likewise, the surgical system 900 of FIG. 9 can be used with other methods. The example methods of the disclosure are particularly well-suited for procedures such as laparoscopic procedures with limited visibility of the tissue to be resected and adjacent anatomy.

Step 1010 can include placing a magnet-attracting portion 970 of a cut guide 926 proximate a first side of a tissue to be treated. In some examples, the magnet-attracting portion 970 can be formed of a material that is both magnetic and electrically conductive (e.g., metal). In other examples, the magnet-attracting portion may include a plurality of materials to provide both magnet attracting characteristics and electrically conductive characteristics. The magnet-attracting portion can be in electrical communication with an electrosurgical generator 958.

Step 1020 can include placing an electrode 966 of a tissue resection device 960 proximate a second side of the tissue to be treated. The tissue resection device 960 can have a magnet 964 coupled adjacent to the electrode 966 and the electrode 966 of the tissue resection device 960 can be in electrical communication with the electrosurgical generator 958.

Step 1030 can include guiding the magnet 964 along a path of the magnet-attracting portion 970 to treat the tissue between the magnet attracting portion 970 and the electrode 966 while delivering electrical energy to a conductive portion, thereby resecting or creating a cut through the tissue.

Variations of method 1000 are not limited to colpotomy procedures, method 1000 can be used for directing in situ guidance of an electrosurgical device in other procedures.

In at least one example, step 1010 can include placing a cut guide proximate a first side of a tissue to be treated, the cut guide having guide portion, such as, but not limited to, a metal ring. The guide portion can be in electrical communication with an electrosurgical generator, wherein the guide portion can include at least one of a magnet and a magnet-attracting material.

In at least one example, step 1020 can include placing an electrode of a tissue resection device having a guide attraction portion such as, but not limited to, the magnet, located adjacent to the electrode proximate to a second side of the tissue to be treated. The tissue resection device can be in electrical communication with the electrosurgical generator. The guide attraction portion can include the other of the magnet and the magnet-attracting material.

In at least one example, step 1030 can include guiding the guide attraction portion along a path of the guide portion to treat the tissue between the guide portion and the electrode while delivering electrical energy to the electrode.

In some examples, the cut guide can be a colpotomy cup and the guide portion can have a circumferential shape. The guide portion can include metal, such as a ferrous metal, and the guide attraction portion can include the magnet. In some examples, the guide portion can include the magnet, and the guide attraction portion can include metal. In some examples, the guide portion can be a metal ring.

The benefits of the systems and methods of the present disclosure can include: 1) improved accuracy of the cut location for challenging surgical procedures such as a colpotomy procedure; 2) increased visibility of a cut location for performing surgical procedures by providing light to a distal end of a cutting device; and 3) improved cut guides, cutting devices and tissue resection devices that reduce the likelihood of inadvertent injury to adjacent tissues, such as injury to a bowel or bladder in a colpotomy procedure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

VARIOUS NOTES AND EXAMPLES

Example 1 is a tissue resection device comprising: an elongate member including a body that extends from a proximal portion to a distal portion and a lumen extending therebetween, a handle coupled to the proximal portion; an end effector coupled to the distal portion, the end effector extending along a longitudinal axis, the end effector including: a first cut guide including an outer support surface that extends from a first proximal end portion to a first distal end portion, wherein the first distal end portion includes, a first outer distal portion; a second cut guide located around the first cut guide, the second cut guide having an inner support surface that extends from a second proximal end portion to a second distal end portion, wherein the second distal end portion includes a second outer distal portion, and wherein the first outer distal portion is located distal of the second outer distal portion, and wherein the first outer distal portion is located farther laterally from the longitudinal axis than the second outer distal portion; and a cutting device located between the outer support surface and the inner support surface; and a cutting device actuator configured to actuate movement of at least a portion of the cutting device to protrude beyond the first outer distal portion and the second outer distal portion, wherein the cutting device is movable in a direction having a longitudinal component and a lateral component when actuated.

In Example 2, the subject matter of Example 1 includes, wherein the second outer distal portion is configured to follow the first outer distal portion when the end effector is inserted into a vagina of a patient.

In Example 3, the subject matter of Examples 1-2 includes, wherein the first outer distal portion is configured to displace a vaginal wall of a patient to a first dimension when inserted into a vagina of the patient, wherein the second outer distal portion is configured to displace the vaginal wall of the patient to a second dimension, and wherein the first dimension is greater than the second dimension.

In Example 4, the subject matter of Examples 1-3 includes, wherein the tissue resection device includes a colpotomy cup assembly, and wherein the first cut guide includes an inner cup portion and the second cut guide includes an outer cup portion.

In Example 5, the subject matter of Examples 1-4 includes, wherein the cutting device includes an insulative central portion at least partially surrounded by a conductive peripheral portion, and wherein at least a portion of the insulative central portion comprises an optically transparent material.

In Example 6, the subject matter of Example 5 includes, wherein the cutting device includes a tip that extends distal of the conductive peripheral portion, and wherein the tip comprises an optically transparent or mostly optically transparent material.

In Example 7, the subject matter of Examples 1-6 includes, an optical pathway configured to carry light received from a proximal light source to an optically transparent tip of the cutting device.

Example 8 is an end effector assembly of a tissue resection device, the end effector assembly comprising: a first cut guide that extends from a first proximal end portion to a first distal end portion along a longitudinal axis, wherein the first distal end portion includes, a first outer distal portion; a second cut guide located around the first cut guide, the second cut guide extends from a second proximal end portion to a second distal end portion, wherein the second distal end portion includes a second outer distal portion, wherein the first outer distal portion is located distal of the second outer distal portion, and wherein the first outer distal portion is located farther laterally from the longitudinal axis than the second outer distal portion; and a cutting device located between the first cut guide and the second cut guide, wherein the cutting device is configured to move relative to at least one of the first cut guide and the second cut guide when actuated.

In Example 9, the subject matter of Example 8 includes, wherein the second outer distal portion is configured to follow the first outer distal portion when the end effector assembly is inserted into a vagina of a patient, wherein the first outer distal portion is configured to displace a vaginal wall of the patient to a first dimension, and wherein the second outer distal portion is configured to displace the vaginal wall of the patient to a second dimension, and further wherein the first dimension is greater than the second dimension.

In Example 10, the subject matter of Example 9 includes, wherein the end effector assembly includes a colpotomy cup assembly, the first cut guide includes an inner cup portion and the second cut guide includes an outer cup portion.

In Example 11, the subject matter of Examples 9-10 includes, wherein the cutting device includes an insulative central portion at least partially surrounded by a conductive peripheral portion, and wherein at least a portion of the insulative central portion comprises an optically transparent material.

In Example 12, the subject matter of Example 11 includes, wherein the cutting device includes a tip that extends distal of the conductive peripheral portion, and wherein the tip comprises an optically transparent or mostly optically transparent material.

In Example 13, the subject matter of Examples 9-12 includes, an optical pathway configured to carry light received from a proximal light source to an optically transparent tip of the cutting device.

Example 14 is an end effector assembly of a colpotomy tissue resection device, the end effector assembly comprising: a first cut guide having a first distal peripheral portion; a second cut guide having a second distal peripheral portion, the second cut guide located around the first cut guide, wherein the first distal peripheral portion is located distal of the second distal peripheral portion, and wherein the first distal peripheral portion is located farther laterally from a longitudinal axis of the end effector assembly than the second distal peripheral portion; and a cutting device located between the first cut guide and the second cut guide, wherein the cutting device is moveable relative to at least one of the first cut guide and the second cut guide.

In Example 15, the subject matter of Example 14 includes, wherein the second distal peripheral portion is configured to follow the first distal peripheral portion when the end effector assembly is inserted into a vagina of a patient, wherein the first distal peripheral portion is configured to displace a vaginal wall of the patient to a first dimension when inserted into the vagina of the patient, wherein the second distal peripheral portion is configured to displace the vaginal wall of the patient to a second dimension, and wherein the first dimension is greater than the second dimension.

In Example 16, the subject matter of Examples 14-15 includes, wherein the end effector assembly includes a colpotomy cup assembly and the first cut guide includes an inner cup portion and the second cut guide includes an outer cup portion, wherein at least one of the inner cup portion and the outer cup portion guides the cutting device.

In Example 17, the subject matter of Examples 14-16 includes, wherein the cutting device includes an insulative central portion at least partially surrounded by a conductive peripheral portion, wherein at least a portion of the insulative central portion comprises an optically transparent material.

In Example 18, the subject matter of Example 17 includes, wherein the cutting device includes a tip that extends distal of the conductive peripheral portion, and wherein the tip comprises an optically transparent or mostly optically transparent material.

In Example 19, the subject matter of Examples 17-18 includes, an optical pathway configured to carry light received from a proximal light source to an optically transparent tip of the cutting device wherein the optical pathway extends through the insulative central portion.

In Example 20, the subject matter of Examples 14-19 includes, an optical pathway configured to carry light received from a proximal light source to an optically transparent tip of the cutting device.

Example 21 is a tissue resection device comprising: a cutting device that extends from a proximal end to a distal end along a longitudinal path, the cutting device including an insulative central portion at least partially surrounded by a conductive peripheral portion, wherein the insulative central portion comprises an optically transparent material; and a cutting guide configured to support the cutting device.

In Example 22, the subject matter of Example 21 includes, wherein the insulative central portion extends along the longitudinal path, and wherein the conductive peripheral portion includes at least one of a first lateral conductive portion and a second lateral conductive portion separated by the insulative central portion.

In Example 23, the subject matter of Example 22 includes, the cutting device further comprising: a conductive tip portion in electrical communication with at least one of the first lateral conductive portion and the second lateral conductive portion.

In Example 24, the subject matter of Example 23 includes, wherein at least a portion of the conductive tip portion includes the optically transparent material.

In Example 25, the subject matter of Examples 21-24 includes, an optical pathway in the insulative central portion, the optical pathway configured to receive light from a proximal light source.

In Example 26, the subject matter of Examples 21-25 includes, an optical pathway extending along the longitudinal path and through the insulative central portion.

In Example 27, the subject matter of Examples 21-26 includes, an optical pathway extending along the longitudinal path and adjacent to the insulative central portion, the optical pathway configured to carry light received from a proximal light source to the distal end of the cutting device.

In Example 28, the subject matter of Examples 21-27 includes, wherein the cutting device comprises optically transparent tip configured to receive light from a proximally located light source and disperse light through the distal end of the cutting device.

In Example 29, the subject matter of Examples 21-28 includes, wherein the cutting device is movable relative to at least a portion of the cutting guide.

Example 30 is a tissue resection device comprising: a cutting device that extends from a proximal end to a distal end along a longitudinal path, the cutting device including an insulative central portion partially surrounded by a conductive peripheral portion, wherein the insulative central portion comprises an optically transparent material that extends distal of the conductive peripheral portion.

Example 31 is a method of in situ guiding an electrosurgical device, such as, but not limited to, performing a colpotomy, the method of in situ guiding the electrosurgical device comprising: placing a metal ring of a colpotomy cup proximate a first side of a tissue to be treated, the metal ring located at a distal end portion of the colpotomy cup, wherein the metal ring is in electrical communication with an electrosurgical generator; placing an electrode of a tissue resection device having a magnet coupled adjacent to the electrode proximate to a second side of the tissue to be treated, wherein the tissue resection device is in electrical communication with the electrosurgical generator; and guiding the magnet along a path of the metal ring to treat the tissue between the metal ring and the electrode while delivering electrical energy to at least one of the metal ring and the electrode.

Example 32 is a tissue resection device comprising: a body that is manipulatable by a user or a machine to position the tissue resection device at a treatment site; an electrode coupled to the body, wherein the electrode is configured to be coupled to an electrosurgical generator to transmit electrical energy to a tissue to be treated; and a magnet coupled to the body and located adjacent to the electrode, wherein the magnet is configured to be attracted to a magnet-attracting portion of a cut guide when the cut guide and the magnet are positioned in contact with opposite sides of the tissue to be treated. In Example 33, the subject matter of Example 32 includes, wherein the magnet induces a magnetic field in that attracts the magnet to the magnet-attracting portion when the magnet is placed a distance in a range between 1 mm-1 cm of the magnet-attracting portion with vaginal tissue disposed between the magnet and the magnet-attracting portion.

Example 34 is a colpotomy resection system comprising: a colpotomy guide configured to be inserted into a vagina of a patient, the colpotomy guide extending from a proximal end to an opening at a distal end, wherein the distal end includes, a conductive rim around the opening, wherein the conductive rim includes a material that attracts magnets, and wherein the conductive rim is configured to be electrically couplable to an electrosurgical generator; and a tissue resection device including a magnet coupled to an adjacent electrode, wherein the tissue resection device is configured to be couplable to the electrosurgical generator, and wherein the magnet is configured to be attracted to the conductive rim when a cervical-vaginal junction of the patient is located between the magnet and the conductive rim.

Example 35 is a method of directing in situ guidance of an electrosurgical device, the method comprising: placing a cut guide proximate a first side of a tissue to be treated, the cut guide having guide portion, wherein the guide portion is in electrical communication with an electrosurgical generator, wherein the guide portion includes, at least one of a magnet and a magnet-attracting material; placing an electrode of a tissue resection device having a guide attraction portion located adjacent to the electrode proximate to a second side of the tissue to be treated, wherein the tissue resection device is in electrical communication with the electrosurgical generator, wherein the guide attraction portion includes the other of the magnet and the magnet-attracting material; and guiding the guide attraction portion along a path of the guide portion to treat the tissue between the guide portion and the electrode while delivering electrical energy to the electrode.

In Example 36, the subject matter of Example 35 includes, wherein the cut guide is a colpotomy cup, wherein the guide portion has a circumferential shape.

In Example 37, the subject matter of Examples 35-36 includes, wherein the guide portion comprises metal, and wherein the guide attraction portion comprises the magnet.

In Example 38, the subject matter of Examples 35-37 includes, wherein the guide portion comprises the magnet, and wherein the guide attraction portion comprises a metal.

In Example 39, the subject matter of Examples 35-38 includes, wherein the guide portion is a metal ring.

Example 40 is at least one machine-readable medium including instructions that, when executed by processing circuitry, cause the processing circuitry to perform operations to implement of any of Examples 1-39.

Example 41 is an apparatus comprising means to implement of any of Examples 1-39.

Example 42 is a system to implement of any of Examples 1-39.

Example 43 is a method to implement of any of Examples 1-39.

What is claimed is:

1. A tissue resection device comprising:

an elongate member including a body that extends from a proximal portion to a distal portion and a lumen extending therebetween, a handle coupled to the proximal portion;

an end effector coupled to the distal portion, the end effector extending along a longitudinal axis, the end effector including:

a first cut guide comprising a first laterally extending base arranged transverse to the longitudinal axis and a first upward extending frustoconical sidewall depending therefrom and defining a continuous outer support surface that extends from a first proximal end portion to a first distal end portion, wherein the first distal end portion includes a first outer distal portion forming a continuous, circular rim surface around the first cut guide;

a second cut guide located around the first cut guide, the second cut guide comprising a second laterally extending base arranged transverse to the longitudinal axis and a second upward extending frustoconical sidewall depending therefrom and defining a continuous inner support surface that extends from a second proximal end portion near the second laterally extending base to a second distal end portion, wherein the second distal end portion includes a second outer distal portion, and wherein the first outer distal portion is located distal of the second outer distal portion, and wherein the first outer distal portion is located farther laterally from the longitudinal axis than the second outer distal portion; and a cutting device located between the continuous outer support surface and the continuous inner support surface; and a cutting device actuator configured to actuate movement of at least a portion of the cutting device to protrude beyond the first outer distal portion and the second outer distal portion, wherein the cutting device is movable in a direction having a longitudinal component and a lateral component when actuated.

2. The tissue resection device of claim 1, wherein the second outer distal portion is configured to follow the first outer distal portion when the end effector is inserted into a vagina of a patient.

3. The tissue resection device of claim 1, wherein the first outer distal portion is configured to displace a vaginal wall of a patient to a first dimension when inserted into a vagina of the patient, wherein the second outer distal portion is configured to displace the vaginal wall of the patient to a second dimension, and wherein the first dimension is greater than the second dimension.

4. The tissue resection device of claim 1, wherein the cutting device includes an insulative central portion at least partially surrounded by a conductive peripheral portion, and wherein at least a portion of the insulative central portion comprises an optically transparent material.

5. The tissue resection device of claim 4, wherein the cutting device includes a tip that extends distal of the conductive peripheral portion, and wherein the tip comprises an optically transparent or mostly optically transparent material.

6. An end effector assembly of a tissue resection device, the end effector assembly comprising:

a first cut guide comprising a first laterally extending base arranged transverse to a longitudinal axis and a first upward extending frustoconical sidewall depending therefrom that extends from a first proximal end portion to a first distal end portion along the longitudinal axis, wherein the first distal end portion includes a first outer distal portion forming a continuous, circular rim surface around the first cut guide;

a second cut guide located around the first cut guide, the second cut guide comprising a second laterally extending base arranged transverse to the longitudinal axis and a second upward extending frustoconical sidewall depending therefrom and defining a continuous inner support surface that extends from a second proximal end portion to a second distal end portion, wherein the second distal end portion includes a second outer distal portion, wherein the first outer distal portion is located distal of the second outer distal portion, and wherein the first outer distal portion is located farther laterally from the longitudinal axis than the second outer distal portion; and a cutting device located between the first cut guide and the second cut guide, wherein the cutting device is configured to move relative to at least one of the first cut guide and the second cut guide when actuated.

7. The end effector assembly of claim 6, wherein the cutting device includes an insulative central portion at least partially surrounded by a conductive peripheral portion, and wherein at least a portion of the insulative central portion comprises an optically transparent material.

8. The end effector assembly of claim 7, wherein the cutting device includes a tip that extends distal of the conductive peripheral portion, and wherein the tip comprises an optically transparent or mostly optically transparent material.

9. The end effector assembly of claim 6, further comprising an optical pathway configured to carry light received from a proximal light source to an optically transparent tip of the cutting device.

10. An end effector assembly of a tissue resection device, the end effector assembly comprising:

a first cut guide comprising a first laterally extending base arranged transverse to a longitudinal axis and a first upward extending frustoconical sidewall depending therefrom and having a first distal peripheral portion forming a continuous, circular rim surface around the first cut guide;

a second cut guide comprising a second laterally extending base arranged transverse to the longitudinal axis and a second upward extending frustoconical sidewall depending therefrom and having a second distal peripheral portion, the second cut guide located around the first cut guide, wherein the first distal peripheral portion is located distal of the second distal peripheral portion, and wherein the first distal peripheral portion is located farther laterally from the longitudinal axis of the end effector assembly than the second distal peripheral portion; and a cutting device located between the first cut guide and the second cut guide, wherein the cutting device is moveable relative to at least one of the first cut guide and the second cut guide.

11. The end effector assembly of claim 10, wherein the second distal peripheral portion is configured to follow the first distal peripheral portion when the end effector assembly is inserted into a vagina of a patient, wherein the first distal peripheral portion is configured to displace a vaginal wall of the patient to a first dimension when inserted into the vagina of the patient, wherein the second distal peripheral portion is configured to displace the vaginal wall of the patient to a second dimension, and wherein the first dimension is greater than the second dimension.

12. The end effector assembly of claim 10, wherein the cutting device includes an insulative central portion at least partially surrounded by a conductive peripheral portion, wherein at least a portion of the insulative central portion comprises an optically transparent material.

13. The end effector assembly of claim 12, wherein the cutting device includes a tip that extends distal of the conductive peripheral portion, and wherein the tip comprises an optically transparent or mostly optically transparent material.

14. The end effector assembly of claim 10, further comprising an optical pathway configured to carry light received from a proximal light source to an optically transparent tip of the cutting device.

15. The end effector of claim 1, wherein the first proximal portion is arranged within the second cut guide, proximal of the second outer distal portion, and laterally nearer the longitudinal axis than the second outer distal portion, and the first outer support surface extends distally and laterally from the first proximal portion, passed the second outer distal portion, out of the second cut guide, and to the first outer distal portion.

16. The end effector of claim 1, wherein first cut guide is a separate component from the second cut guide and is spaced along the elongate member by a distance from the second cut guide, the first and second cut guides being directly coupled to the elongate member.

17. The tissue resection device of claim 1, wherein the second laterally extending base is separated from the first laterally extending base by a gap and, wherein, a portion of the cutting device is moveable along the longitudinal axis and within the gap from a retracted position to a deployed position.

18. The end effector assembly of claim 6, wherein the second laterally extending base is separated from the first laterally extending base by a gap and, wherein, a portion of the cutting device is moveable along the longitudinal axis within the gap from a retracted position to a deployed position.

19. The end effector assembly of claim 10, wherein the second laterally extending base is separated from the first laterally extending base by a gap and, wherein, a portion of the cutting device is moveable along the longitudinal axis and within the gap from a retracted position to a deployed position.

* * * * *